US006287332B1

(12) United States Patent
Bolz et al.

(10) Patent No.: US 6,287,332 B1
(45) Date of Patent: Sep. 11, 2001

(54) IMPLANTABLE, BIORESORBABLE VESSEL WALL SUPPORT, IN PARTICULAR CORONARY STENT

(75) Inventors: Armin Bolz, Erlangen; Thomas Popp, Nürnberg, both of (DE)

(73) Assignee: Biotronik Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/339,927

(22) Filed: Jun. 25, 1999

(30) Foreign Application Priority Data

Jun. 25, 1998 (DE) ............................. 198 28 245
Dec. 10, 1998 (DE) ............................. 198 56 983

(51) Int. Cl.$^7$ ................. A61F 2/02; A61F 2/04; A61F 2/06
(52) U.S. Cl. .............. 623/1.15; 623/1.12; 623/1.38; 623/1.49
(58) Field of Search ................... 623/1.1, 1.12, 623/1.15, 1.38, 1.49

(56) References Cited

U.S. PATENT DOCUMENTS

| 5,061,275 | 10/1991 | Wallsten et al. . |
| 5,477,864 | 12/1995 | Davidson . |
| 5,620,452 | 4/1997 | Yoon . |
| 5,649,977 | 7/1997 | Campbell . |
| 5,690,670 | 11/1997 | Davidson . |

FOREIGN PATENT DOCUMENTS

| 4207557 | 9/1993 | (DE) . |
| 4339524 | 1/1995 | (DE) . |
| 4336209 | 3/1995 | (DE) . |
| 4411974 | 10/1995 | (DE) . |
| 19634241 | 2/1998 | (DE) . |
| 19653721 | 4/1998 | (DE) . |
| 0601804 | 12/1993 | (EP) . |
| 0788802 | 8/1997 | (EP) . |
| 0804934 | 11/1997 | (EP) . |
| 9307924 | 4/1993 | (WO) . |
| WO 99/03515 A2 | 1/1999 | (WO) . |

Primary Examiner—David H. Willse
Assistant Examiner—Choon Koh
(74) Attorney, Agent, or Firm—Browdy & Neimark

(57) ABSTRACT

An implantable, bioresorbable vessel wall support, in particular a coronary stent, comprises a combination of metal materials which dissolves in the human body without any harmful effects on the person that wears the implant. The combination of metal materials can be an alloy or a local galvanic element.

20 Claims, No Drawings

IMPLANTABLE, BIORESORBABLE VESSEL WALL SUPPORT, IN PARTICULAR CORONARY STENT

BACKGROUND OF THE INVENTION

1. Field of the Invention

The invention relates to an implantable, bioresorbable vessel wall support, in particular a coronary stent.

2. Background Art

As for the background of the invention, so-called "vessel wall supports" or "stents"—as they are called in the technical language—are used in the therapy of stenoses, i.e. pathologically constricted passages of a coronary vessel. To this end, such a coronary stent is introduced transvenously into the human body by means of a catheter and delivered through the coronary system to the treatment site in the heart. In this condition of introduction and delivery, the stent must have an outside diameter of not more than approximately 1 mm for sufficient mobility. Having reached the stenotic passage of the coronary vessel, the stent is durably expanded for the stenosis to be removed. By means of the catheter on which it has been introduced, the stent is radially expanded to a diameter of approximately 4 mm, which is accompanied with plastic deformation. To this end, the catheter is a balloon catheter, in which the lengthwise section which supports the stent is dilated in a manner similar to a balloon by the application of superpressure by means of salt solution.

Conventional implanted stents consist of a metal material suitable for the medical use and which may be provided with an anticoagulant layer for the avoidance of thrombosis problems. A drawback of these durably implanted stents resides in the detectable permanent irritation of the tissue surrounding the stent, since the stent, because of its rigidity, does not perform the flexions, caused by heartbeat, of the coronary vessel it supports.

Furthermore, attention is drawn to the fact that as a rule the support by a stent for the expansion of a stenosis is required only for a period of some months. Afterwards, the part of the vessel affected by stenosis would remain open even without any support.

For the elimination of the afore-mentioned problems, stents have been proposed to be manufactured from bioresorbable materials which decompose in the human body in the course of few months. A method for the manufacture of such bioresorbable coronary stents is known for instance from U.S. patent application Ser. No. 08/733,172. In this case, a stent blank of homogeneous polymeric structure is built up from a viscous solution of poly-β-hydroxybutanoic acid as a bioresorbable polymeric material in a solvent by successively coating a male mold core with layers of the polymer solution in several steps by precipitation of the polymeric material by the solvent being evaporated and by the layer previously precipitated being dissolved at least partially. This stent blank is then drawn off the male mold core and subsequently treated to finish the shaping of the stent.

It is true that bioresorbable coronary stents of polymeric materials have the desired biological resorbability and biocompatibility. However, problems are posed by the often insufficient mechanical properties such as a lack of plastic deformability of this stent. Upon dilatation to as much as four times the diameter, this will lead to fissuring with the consequence of reduced mechanical stability and a high degree of re-deformation. This means that for a final diameter of 4 mm, the maximum expansion must be clearly higher, which again leads to a further increase of fissuring accompanied with corresponding destabilization of the stent.

SUMMARY OF THE INVENTION

To solve these problems, the invention provides to manufacture the vessel wall support of a combination of metal materials which decomposes in the human body without any harmful effects on the person who wears the implant. The combination of metal materials is to be designed such that the material of the vessel wall support dissolves at a certain decomposition rate and without the production of bioincompatible decomposition products. A vessel wall support of this type combines the advantageous mechanical properties of metal stents with the bioresorbability of polymer based stents.

In the first fundamental embodiment of the invention, the combination of metal materials is a metal alloy, the selection of the alloy constituents—as explained in detail below—serving to attain the prerequisite of biocompatible decomposition. Consequently, the metal alloy has to consist of a combination of material that will decompose in the body comparatively rapidly—within a period of some months—forming harmless constituents, which can be defined by the palpable term of "biocompatible corrosion".

For correspondingly uniform corrosion to be obtained, such an alloy comprises a component A which covers itself with a protective oxide coat. This component A is selected from one or several metals of the group of magnesium, titanium, zirconium, niobium, tantalum, zinc or silicon. For uniform dissolution of the mentioned oxide coat to be attained, a component B is added to the alloy, possessing sufficient solubility in blood or interstitial fluid, such as lithium sodium, potassium, calcium, iron or manganese.

The mentioned elements are suitable because they are present in the human body anyway—such as magnesium, zinc, sodium, potassium, calcium, iron and manganese—or are know to be nontoxic—such as titanium, zirconium, niobium, tantalum, silicon and lithium. The combination of a passivating and a soluble component ensures a timely and uniform decomposition into biocompatible breakdown products. The corrosion rate can be regulated through the ratio of the two components.

In an especially preferred manner, the alloy is to be composed so that the corrosion products are soluble salts, such as sodium, potassium, calcium, iron or zinc salts, or that non-soluble corrosion products, such as titanium, tantalum or niobium oxide originate as colloidal particles. The corrosion rate is adjusted by way of the composition so that gases, such as hydrogen which evolves during the corrosion of lithium, sodium, potassium, magnesium, calcium or zinc, dissolve physically, not forming any macroscopic gas bubbles.

Furthermore, for instance a so-called super light alloy of lithium and magnesium known from aeronautics can be used as a possible alloy, which is however optimized with a view to increased fatigue durability and reduced avidity for the field of application mentioned above. The magnesium-lithium ratio is in the range of 60:40, fatigue durability being increased by the addition of further components such as zinc or by gassing by hydrogen. Also, special melting and forging methods are used to increase the fatigue durability.

For putting the present invention into practice, lithium-magnesium alloys can be used, which have a lower fatigue durability during conventional treatment and in the body sphere. Lithium hydroxide and magnesium hydroxide are to be expected as decomposition products, which can both be considered non-toxic and biocompatible.

Problems posed by the mentioned lithium-magnesium alloy reside in that the decomposition products lithium hydroxide and magnesium hydroxide are poorly soluble and with the absorption of carbon dioxide convert to the carbonates which are also poorly soluble. In particular lithium hydroxide is very voluminous in this case. The corrosion products encrust on the stent, these crusts being able to occupy a multiple of the volume of the stent.

In this regard, other combinations of alloys are more suitable, for example a sodium-magnesium alloy. Since sodium hydroxide as a corrosion product possesses a high solubility, this alloy decomposes without voluminous encrusting. Sodium dissolves and magnesium hydroxide forms a fine precipitate which may deposit without risk in the developing vascular skin, the so-called intima.

Another preferred embodiment of a decomposable combination of metal materials is a zinc-titanium alloy, the percentage by weight of which is in the range of 0.1% to 1%. This combination precludes the comparatively strong crystalline growth of zinc as a material used, which would cause a comparatively brittle and fragile behavior of the vessel wall support. When the material is worked, the addition of titanium leads to the formation of a $Zn_{15}Ti$ phase on the crystal boundaries which precludes any further crystalline growth. This reduction of the grain size generally improves the ductility, in particular the elongation at rupture—i.e. the percentage elongation of the material under mechanical load as far as to the rupture thereof.

If gold is added to this alloy at a percentage by weight of 0.1% to 2%, a further reduction of the grain size is attained when the material cures. This further improves the tensile strength of the material.

In addition to the realization of the combination of metal materials in the form of a metal alloy, another fundamental embodiment may be the design of the combination of metal materials as an electrochemical local element. On the one hand, this element consists of a substantially pure metal which constitutes the body of the vessel wall support and on the other hand, of a local electrode of a second metal which is in contact therewith. The local electrode combines with the support body to form a local element in which the potential of the support body is displaced, corresponding to the electron-chemical series. The contact voltage originating causes the corrosion process of the stent body. The corrosion rate and thus the decomposition rate of the stent can be controlled by way of the size of the surface of contact between the corrodible stent body and the local electrode connected thereto or by the selection of the participant element.

In keeping with two alternative embodiments, the participant element can be a coat on the support body or an individual metal part attached to the support body for example by welding. In this case, the local electrodes may also serve as X-ray markers, having a typical double function.

Details of the invention will be explained below, based on three preferred exemplary embodiments:

DESCRIPTION OF PREFERRED EMBODIMENTS

EXAMPLE 1

A bioresorbable metal stent is made from an alloy in which the component A consists of zinc and the component B of calcium. The weight ratio that zinc bears to calcium amounts to at least 21:1. This Zn—Ca alloy is an alloy in which the corrosion products of both components are soluble salts, which is of special advantage in the case of the present field of application. Calcium hydroxide possesses so high a solubility that the solubility product is not transgressed during slow corrosion over several weeks or months. The coronary hydroxide is transported in dissolved form by the blood and subjected to metabolism. The corrosion rate is regulated by way of the ratio of the two components, which can be detected by simple tests.

So as to improve the mechanical properties of the stent, such as ductility, hardness and tensile strength, corresponding alloy components can be added in low concentrations. For instance, the nonmetal phosphorus might be added to the alloy in the order of a few percents.

EXAMPLE 2

The support body of a bioresorbable metal stent consists of pure zinc, which dissolves—as electroplating tests show—without the production of gases and without the formation of oxide at external currents of some mA.

For the generation of such an "external" current, a local element, for example in the form of a gold electrode, is installed on the stent by electroplating or by laser welding, cooperating as a local electrode with the support body to produce a contact voltage, since the gold electrode assumes approximately the potential of the zinc electrode and the potential of the zinc electrode becomes slightly more positive. A corresponding current results, leading to active zinc dissolution. Corresponding cathodic currents flow on the gold electrode. The exchange current as a whole is determined by the surface of the gold electrode because of the low cathodic currents of the gold electrode. The corrosion rate can be adjusted by this mechanism via the surface of the local element.

Tests have shown that tin in the case of a local element of gold on zinc, an exchange current arises after few minutes and remains constant for several days. In this regard, a constant corrosion rate is attainable and a stent of for instance 10 mg of weight will dissolve within approximately 30 to 40 days at a corrosion current of 10 $\mu A$.

EXAMPLE 3

A bioresorbable metal stent is made form a ZnTi alloy with a Ti weight percentage of 0.1% to 1%. In a further improved embodiment of this example, a precious metal in the form of gold can be added at a weight percentage of 0.1% to 2%, the Ti weight percentage remaining invariable, so that the stent consists of a ZnAuTi alloy.

The two above-mentioned alloys of example 3 also exhibit a biocompatible decomposition behavior and are consequently regarded as bioresorbable metal stents.

What is claimed is:

1. An implantable, bioresorbable vessel wall support, wherein the vessel wall support comprises a combination of metal materials that decomposes in a human body without any harmful effects on the wearer of the implantable, bioresorbable vessel wall support.

2. A vessel wall support according to claim 1, wherein the combination of metal materials is a metal alloy consisting at least of a first component which forms a protecting passivation coat and of a second component which ensure sufficient corrosion of the alloy.

3. A vessel wall support according to claim 2, wherein the first component is at least one metal selected from the group consisting of magnesium, titanium, zirconium, niobium, tantalum, zinc and silicon and the second component is at least one metal selected from the group consisting of lithium, sodium, potassium, manganese calcium and iron.

4. A vessel wall support according to claim 2, wherein the components of the metal alloy are selected such that corrosion products originate as a particle kind selected from the group consisting of soluble salts, very fine particles, and colloidal particles.

5. A vessel wall support according to claim 2, wherein the components of the metal alloy are selected such that they corrode at such a rate that gases arising during the corrosion physically dissolve in a body fluid which acts on the vessel wall support.

6. A vessel wall support according to claim 2, wherein the alloy contains zinc as corrosion-inhibiting component A.

7. A vessel wall support according to claim 6, wherein the alloy is a zinc-calcium alloy.

8. A vessel wall support according to claim 7, wherein a zinc-calcium weight ratio in the alloy is at least 21:1.

9. A vessel wall support according to claim 2, wherein the alloy is exposed to hydrogen for corrosion inhibition.

10. A vessel wall support according to claim 2, wherein phosphorus is added to the alloy.

11. A vessel wall support according to claim 1, wherein the combination of metal materials is an alloy of zinc and titanium with a weight percentage of titanium of 0.1% to 1%.

12. A vessel wall support according to claim 11, wherein gold is added as a further component to the zinc-titanium alloy at a weight percentage of 0.1% to 2%.

13. A vessel wall support according to claim 1, wherein the combination of metal materials is designed as an electrochemical local element which is formed by a support body of the vessel wall support of a substantially pure first metal on the one hand and on the other hand by a local electrode of a second metal which is in contact therewith and leads to a contact voltage.

14. A vessel wall support according to claim 13, wherein the local electrode is a coat on the support body.

15. A vessel wall support according to claim 13, wherein the local electrode is a metal part attached to the support body.

16. A vessel wall support according to claim 13, wherein the support body consists of zinc.

17. A vessel wall support according to claim 13, wherein the local electrode consists of a precious metal.

18. A vessel wall support according to claim 3, wherein said alloy further comprises phosphorus.

19. A vessel wall support according to claim 6, wherein said alloy further comprises phosphorus.

20. A vessel wall support according to claim 14, wherein the coat which constitutes the local electrode is deposited by one process selected from electroplating and sputtering.

* * * * *